United States Patent [19]

Slaugh

[11] 4,293,723

[45] Oct. 6, 1981

[54] CONVERSION OF ISOBUTENE TO AROMATICS OR POLYISOBUTYLENE WITH MODIFIED GAMMA ALUMINA COMPOSITION

[75] Inventor: Lynn H. Slaugh, Houston, Tex.

[73] Assignee: Shell Oil Company, Houston, Tex.

[21] Appl. No.: 142,591

[22] Filed: Apr. 21, 1980

Related U.S. Application Data

[62] Division of Ser. No. 61,221, Jul. 27, 1979, Pat. No. 4,235,756.

[51] Int. Cl.$^3$ .......................... C07C 2/04; B01J 21/04
[52] U.S. Cl. .................................. 585/407; 208/135; 252/463; 423/628; 585/415; 585/512; 585/521; 585/533

[58] Field of Search .............. 585/407, 415, 510, 512, 585/520, 521, 532, 533; 252/463; 423/628

[56] References Cited

U.S. PATENT DOCUMENTS

| | | | |
|---|---|---|---|
| 3,600,129 | 8/1971 | Vesely et al. | 585/374 |
| 4,112,011 | 9/1978 | Kolombos | 585/415 |
| 4,169,865 | 10/1979 | Bamforth et al. | 585/407 |

*Primary Examiner*—Delbert E. Gantz
*Assistant Examiner*—G. E. Schmitkons

[57] ABSTRACT

A novel aluminous composition prepared by impregnating porous gamma alumina with aluminum hydride and subsequently heating the impregnated alumina to a temperature of from about 300° C. to about 900° C. in a non-oxidizing environment. The composition is useful as a catalyst in reactions catalyzed by acid catalysts.

2 Claims, No Drawings

CONVERSION OF ISOBUTENE TO AROMATICS OR POLYISOBUTYLENE WITH MODIFIED GAMMA ALUMINA COMPOSITION

This is a division of application Ser. No. 061,221, filed July 27, 1979, now U.S. Pat. No. 4,235,756, issued Nov. 25, 1980.

BACKGROUND OF THE INVENTION

1. Field of the Invention

This invention relates to novel aluminous compositions prepared by reacting gamma alumina with aluminum hydride. These compositions are useful as catalysts, particularly as catalysts for acid catalyzed reactions.

2. Background of the Invention

Aluminum hydride has been decomposed to produce aluminum metal coatings on alumina. See U.S. Pat. No. 3,501,333 issued Mar. 17, 1970. These processes are typically low temperature processes, below 250° C. The instant compositions contain no aluminum metal. The compositions of the instant invention have signficantly altered catalyst properties over conventional alumina catalysts. They find use for catalyzing acid catalyzed reactions.

SUMMARY OF THE INVENTION

Unique aluminous materials are prepared by impregnating gamma alumina with solutions of aluminum hydride, and subsequently heating the impregnated aluminas in a non-oxidizing environment to temperature of from about 300° to about 900° C. These materials having highly acid sites and are useful as catalysts and catalyst supports for acid catalyzed reactions.

DESCRIPTION OF THE PREFERRED EMBODIMENTS

The gamma used in the application to prepare the instant compositions are readily available commercially and are frequently used as catalysts and catalyst supports. The term "gamma alumina" as used herein refers to the intermediate forms of alumina encountered during the thermal decomposition of the hydrated aluminas and sometimes during that of other aluminum compounds before the appearance of alpha alumina, which constitutes the stable phase above 1100° C. The gamma alumina may contain minor proportions of other materials without departing from the scope of the invention such as, for example, silica and carbon. Prior to use the gamma alumina should be substantially free of adsorbed water, i.e. "substantially dehydrated". The residuum of chemically bound water, i.e., water of hydration, is not harmful to the process of this invention. The adsorbed or free water is removed by heating the gamma alumina at temperatures from about 200° to about 900° C. prior to contact with the aluminum hydride impregnating solution. Any environment that will provide for drying is suitable, such as air, vacuum, inert gas such as nitrogen, etc. The dried alumina should be kept away from a humid atmosphere after drying. A convenient drying atmosphere is that used to heat the impregnated alumina, such as nitrogen.

The aluminum hydride suitable for use in this invention is prepared commercially by reacting at room temperature lithium aluminum hydride and aluminum chloride in diethyl ether (Et$_2$O). The product is isolated in high yield by decanting and drying at room temperature under vacuum. The product is analyzed as AlH$_3$.$\frac{3}{8}$Et$_2$O. For purposes of this invention the aluminum hydride is dissolved in a suitable organic solvent. The prime requirement on the solvent is that it be anhydrous and non-hydroxyl containing since water and alcohol react with aluminum hydride. Suitable solvents are for example, ethers, such as diethyl ether, tetrahydrofuran, pyridine, benzene, toluene, chloroform and the like.

To prepare the compositions of the instant invention, gamma alumina, suitably dried of adsorbed water is contacted with a solution of aluminum hydride in appropriate proportions as to provide the desired amount of aluminum hydride per unit weight of gamma alumina. A suitable method of impregnation is described in U.S. Pat. No. 3,146,209, issued Aug. 25, 1964. The impregnated gamma alumina is dried of solvent and then heated (activated) in a non-oxidizing atmosphere at temperatures of from about 300° C. to about 900° C., more preferably at temperatures of from 450° to about 750° C. The drying step is preferably carried out in the initial stages of the heating step. Suitable non-oxidizing atmospheres are inert atmospheres such as nitrogen, helium, argon, vacuum etc, and reducing atmospheres such as hydrogen, carbon monoxide, etc. Drying temperatures are not critical and depend on the particular solvent and will range from about 60 to about 100% of the boiling point (absolute). Drying and heating times are not critical and depend upon temperatures. They are readily determined by simple experimentation. Five minutes to one hour are usually sufficient. Typically the amount of aluminum hydride (measured as aluminum metal) added will range from about 0.01 to about 35 preferably from about 0.1 to about 25 and more preferably from about 1 to about 10 percent by weight of the total composition.

Different reactions will require different optimum amounts of aluminum hydride added. For example, for the dehydrocoupling of isobutene to aromatics the aluminum hydride added will range from about 2 to about 10, preferably from about 3 to about 7 percent by weight of aluminum per total composition.

The composition of this invention finds use for catalyzing acid catalyzed reactions. The compositions of this invention are more acid than conventional alumina. While the exact physical structure of the compositions which provide this enhanced activity is not known, it is speculated that the decomposition of the aluminum hydride on the gamma alumina surface produces localized Lewis acid sites having an atomic ratio of oxygen to aluminum lower than the normal ratio. Analysis of the instant composition indicated no aluminum metal had been deposited on the alumina and an insignificant amount of residual alumina hydride remained. These findings are consistent with the above theory of aluminum hydride reacting with the gamma alumina.

The preparation of the compositions of this invention and their utilization as catalysts will be further described below by the following illustrative embodiments which are provided for illustration and are not to be construed as limiting the invention.

Illustrative Embodiments

Composition Preparation

Gamma alumina (Kaiser alumina A-201, surface area 365 m$^2$/g, pore volume 0.42 cc/gm, 20 to 30 mesh) was pretreated in dry nitrogen at 700° C. for about 10 minutes. Exposure of the support to air was avoided. In a glove box with a dry nitrogen atmosphere, 5 grams of the dried support was impregnated with a solution prepared by dissolving 0.4 grams of $AlH_3 \cdot \frac{3}{8}(CH_3CH_2)_2O$ in 8 milliliters of tetrahydrofuran. The impregnated material was placed in a vycor tube and dry nitrogen passed over the catalyst as the temperature was increased in 50° C. intervals (15 minutes at each temperature) to 500° C. and held at this temperature for 15 minutes. The finished compositon was allowed to cool without exposure to air.

Similar compositions were prepared from gamma aluminas from CCI (surface area 250 m²/g, pore vol. 0.8 cc/gm, 20 to 30 mesh) using the above techniques.

Similar compositions were made by activating at 550° C. and 700° C.

Utilization as Catalysts

Illustrative but not all inclusive examples of the use of the instant compositions as catalysts are provided below.

To illustrate the use of the compositions of this invention as catalysts they were tested for catalytic activity for the dehydrocoupling of isobutene to aromatics. Compositions according to this invention were prepared as described above with different aluminas and differing amounts of added aluminum (examples 1-4). These were compared to an alpha alumina support (example 5), a neat gamma alumina support (example 6), a gamma alumina support impregnated with aluminum nitrate rather than aluminum hydride (example 7), a carbon support impregnated with aluminum hydride (example 8) and an activated carbon support (example 9). The results are shown in Table I.

amounts of $C_1$-$C_4$ hydrocarbons (the $C_2$'s and $C_3$'s were mainly olefins). When the amount of $AlH_3$ placed on the $Al_2O_3$ was increased from 3.8% wt to 7.4% wt, the conversion dropped to 43%, but the aromatics increased to 34.8% (example 2). Low levels of $AlH_3$ did not produce a catalyst significantly different from neat $Al_2O_3$ (example 3) for this reaction.

The catalyst activity appears somewhat dependent upon the support surface area. Example 1 with a surface area of about 365 m²/g and Example 4 with a surface area of 250 m²/g were both quite active, but gave somewhat different product distributions. On the other hand, $AlH_3$ deposited on alpha alumina (low surface area) had little activity.

A catalyst (example 7) prepared by impregnating aluminum with aluminum nitrate and activated at 550° C. showed almost no activity illustrating that impregnation with aluminum hydride is critical to preparing the compostion of the invention.

If, as postulated, Lewis acid sites are indeed generated as the $AlH_3$ decomposes and reacts with the support upon heating in an inert atmosphere, one would not expect good catalysts to result from $AlH_3$ on activated carbon, a non-oxidic support. Examples 8 and 9 show there is little effect from the $AlH_3$ when on activated carbon, since both carbon and $AlH_3$/C similarly activated under nitrogen at 550° C. behaved about the same. Mainly isobutane and coke were formed.

The above experiment illustrates the use of the compositions of this invention as catalysts for dehydocoupling isobutene to aromatics in the temperature range of 450° to 600° C. At lower reaction temperatures (75°-150)° C. the composition of this invention oligom-

TABLE I

| | | Conversion of Isobutene Reaction Temperature - 500° C. GHSV - 600 | | | | | | | | |
|---|---|---|---|---|---|---|---|---|---|---|
| | | Conv. of i-$C_4H_8$ % | Selectivity, Mole % (based on $C_4$ equivalents)[e] | | | | | | | |
| Example | Catalyst | | $CH_4$ | $C_2$'s | $C_3$'s | i-butane | n-butane | n-butenes | benzene + toluene | xylenes | total aromatics |
| 1 | $AlH_3$/A-201 $Al_2O_3$[b] 3.8% wt added Al | 79 | 10.1 | 4.4 | 14.2 | 25.3 | 6.4 | 21.8 | 9.8 | 4.8 | 17.7 |
| 2 | $AlH_3$/A-201 $Al_2O_3$[b] 7.4% wt added Al | 43 | 7.3 | 3.2 | 17.9 | 7.7 | 0.1 | 28.8 | 13.2 | 13.6 | 34.8 |
| 3 | $AlH_3$/A-201 $Al_2O_3$[b] 2% wt added Al | 16 | 1.5 | 1.0 | 1.8 | 6.4 | 0.5 | 79.4 | 2.3 | 4.4 | 9.2 |
| 4 | $AlH_3$/$Al_2O_3$[c] 3.8% wt added Al | 57 | 3.4 | 2.9 | 7.6 | 7.3 | 1.9 | 48.1 | 7.4 | 13.6 | 28.7 |
| 5 | $AlH_3$/SCS-9 $Al_2O_3$[d] 3.8% wt added Al | 1.2 | — | — | — | — | — | — | — | — | — |
| 6 | KAISER A-201 $Al_2O_3$[b] | 9 | 3 | 0.5 | 3.9 | 9.5 | 0.2 | 71.1 | 4.6 | 7 | 11.6 |
| 7 | $Al(NO_3)_3$/A-201 $Al_2O_3$[b] 4.2% wt added Al | trace | — | — | — | — | — | — | — | — | — |
| 8 | $AlH_3$/C 2.7% wt added Al | 54 | 3.4 | 0.6 | 2.2 | 85.0 | — | 1.0 | 7.5 | — | ~8 |
| 9 | Activated C | 41 | 3.6 | 0.6 | 5.2 | 83.2 | — | 2.0 | 5.6 | — | ~6 |

[a]All materials were activated by heating in a stream of nitrogen at 550° C.
[b]KAISER KA201 $Al_2O_3$ (surface area 365 m²/g.) Example 7 was impregnated with $Al(NO_3)_3$ and calcined inder $N_2$ to 550° C.
[c]CCI alumina with surface area 250 m²/g
[d]SCS-9 $Al_2O_3$ is a Pechiney alpha-alumina product with a surface area of 9 m²/g.
[e]$C_2$'s and $C_3$'s were mainly olefins.

From the data it can be seen that the impregnation of gamma alumina with aluminum hydride does indeed significantly alter the properties of alumina, producing a new composition-of-matter. At 500° C. a neat gamma alumina, example 6, converted only 9 percent of the isobutene feed to a mixture of $C_1$-$C_4$ hydrocarbons and aromatic compounds (11.6%); n-butenes were the main product. On the other hand, $AlH_3$/$Al_2O_3$ (3.8 wt% $AlH_3$ as Al) converted 79% of the isobutene (example 1) to a mixture containing 17.7% aromatics and substantial erize isobutene to $C_8$, $C_{12}$ and $C_{16}$ olefins. The $C_{16}$ olefins were formed at the lower temperature range only.

What is claimed is:

1. A process for dehydrocoupling isobutene to aromatics which comprises contacting the isobutene at about 450° C.-650° C. with an aluminous composition prepared by a process which comprises impregnating a substantially dehydrated gamma alumina with aluminum hydride dissolved in an anhydrous, non-hydroxyl containing organic solvent, drying the impregnated alumina to remove the solvent and subsequently heating the impregnated alumina at a temperature of about 300° to about 900° C. in a nonoxidizing atmosphere wherein the aluminum hydride added ranges from about 3 to about 7 percent by weight measured as aluminum metal.

2. A process for oligomerizing isobutene to a mixture of $C_8$, $C_{12}$ and $C_{16}$ olefins which comprises contacting the isobutene at about 75°–150° C. with an aluminous composition prepared by a process which comprises impregnating a substantially dehydrated gamma alumina with aluminum hydride dissolved in an anhydrous, non-hydroxyl containing organic solvent, drying the impregnated alumina to remove the solvent and subsequently heating the impregnated alumina at a temperature of about 300° to about 900° C. in a nonoxidizing atmosphere.

* * * * *